| United States Patent [19] | [11] Patent Number: 4,673,566 |
| --- | --- |
| Goosen et al. | [45] Date of Patent: Jun. 16, 1987 |

[54] MICROENCAPSULATION OF LIVING TISSUE AND CELLS

[75] Inventors: Mattheus F. A. Goosen; Geraldine M. O'Shea, both of Toronto; Anthony M. Sun, Willowdale, all of Canada

[73] Assignee: Connaught Laboratories Limited, Willowdale, Canada

[21] Appl. No.: 613,780

[22] Filed: May 24, 1984

Related U.S. Application Data

[63] Continuation-in-part of Ser. No. 501,445, Jun. 6, 1983, abandoned.

[30] Foreign Application Priority Data

Jun. 1, 1983 [CA] Canada ................................. 429460

[51] Int. Cl.$^4$ ........................ A61K 9/50; A61K 37/00
[52] U.S. Cl. ...................................... 424/19; 424/93; 424/110; 435/1; 435/178; 435/180; 435/240; 604/890; 604/891
[58] Field of Search ..................... 424/95, 110, 21, 16, 424/19, 31, 32, 35, 93; 435/240, 241, 1; 604/890, 891

[56] References Cited

U.S. PATENT DOCUMENTS

| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |

OTHER PUBLICATIONS

Biocompatibility and Immunological Studies of Microencapsulation with Cross Linked Alginate Capsules, pp. 563–564, May 1982; Transplantation vol. 33, No. 5.
Microencapsulated Islets as Bioartiricial Endocrin Pancreas, by F. Lim & A. Sun Science, 11/21/80, vol. 210, pp. 908–910.
Encapsulation of Viable Tissue, F. Lim, patent application, filed Oct. 23, 1978, now abandoned (U.S. Ser. No. 953,413).
Nagaoka et al., Abstract No. 67044943, Cell Growth on Hydrogel Membranes with Relation to Surface Properties and Permeability of the Membranes.
Levine et al., Abstract No. 18030624, Parameters Affecting Cell Growth on Reduced Charge Microcarriers.
Levine et al., Abstract No. 68044855, Optimization of Growth Surface Parameters in Microcarrier Cell Culture.
Sugimoto et al., Cell Locomotion on Differently Charged Substrates Effects of Substrate Char on Locomotive Speed of Fibroblastic Cells, Abstract No. 68033245.
Boehm et al., Abstract No. 63011978, Reversible Hyperplasia and Hypertrohpy of the Mouse Liver Induced by a Functional Charge with Pheno Barbital.
M. Kierstan et al., The Immobilization of Microbial Cells, Subcellular Organelles, and Enzymes in Calcium Alginate Gels, Biotechnology and Bioengineering, vol. XIX, pp. 387–397 (1977).
U. Hackel, et al., Immobilisation of Microbial Cells in Polymeric Matrices, European J. Appl. Microbiol. 1,291–293 (1975).
K. Mosbach et al., Entrapment of Enzymes and Microorganisms in Synthetic Cross-Linked Polymers and Their Application in Column Techniques, Acta Chemica Scandinavica 20 (1966) 2807–2810.

*Primary Examiner*—Sam Rosen

[57] ABSTRACT

Living tissue or cells, for example, islets of Langerhans, are microencapsulated for implantation in the body for long term treatment of diabetes or other disease requiring organ transplantation. The microcapsules take the form of a biocompatible semi-permeable hydrogel membrane based on polylysine which permits the passage of materials and oxygen to the cells and metabolic products from the cells while retaining the cells encapsulated. The biocompatible semi-permeable membrane has an outer negatively-charged surface, which, combined with a controlled thickness of polylysine of molecular weight from 10,000 to 30,000 daltons, imparts to the microcapsules the ability to maintain long term effectiveness.

29 Claims, No Drawings

MICROENCAPSULATION OF LIVING TISSUE AND CELLS

REFERENCE TO RELATED APPLICATION

This application is a continuation-in-part of our copending U.S. patent application Ser. No. 501,445 filed June 6, 1983 now abandoned.

FIELD OF INVENTION

The present invention is concerned with the microencapsulation of living tissue or individual cells.

BACKGROUND TO THE INVENTION

Various attempts have been made to microencapsulate biologically-active macromolecules, tissue and individual cells so that they remain viable and in a protected state within a semi-permeable membrane which permits passage of low molecular weight substances, such as nutrients and oxygen, but not of high molecular weight substances, such as, proteins and cells. However, none of these attempts has been successful in providing microcapsules in which tissue or cells enclosed within the semi-permeable membrane are able to survive in an animal body for longer than 2 to 3 weeks, which severely limits the utility of the products in the treatment of diseases requiring organ transplantation, such as diabetes.

In "Semipermeable Microcapsules" by T. M. S. Chang, Science, 146, 1964, 524 to 525, there is described the microencapsulation of erythrocyte hemolysate and urease in semi-permeable polyamide (nylon) membranes. These microcapsules did not survive for long when injected into the blood stream. Papers have described the preparation of semi-permeable microcapsules containing microbial cells and viable red blood cells, namely K. Mosbach and R. Mosbach, Acta Chem. Scand., 20, 1966, 2807 to 2812 and T. M. S. Chang, F. C. MacIntosh and S. G. Mason, "Semi-permeable Aqueous Microcapsules", Can. J. Physiol. and Pharmacology, 44, 1966, 115 to 128. The Chang et al article mentions for the first time the possibility of using injections of encapsulated cells for organ replacement therapy.

The next significant development was the use of calcium and aluminum alginate gels for the immobilization of microbial cells and enzymes. The cells were immobilized under extremely mild conditions, thus maintaining their viability. This work was described in V. Hackel, J. Klein, R. Megret and F. Wagner, Europ. J. Appl. Microbiol., 1, 1975, 291 to 296 and M. Kierstan and C. Bucke, "The Immobilization of Microbial Cells, Subcellular Organelles, and Enzymes in Calcium Alginate Gels", Biotechnology and Bioengineering, 19, 1977, 387 to 397.

Subsequently, viable tissue and cells were immobilized in alginate droplets coated with polylysine (F. Lim and R. D. Moss, "Microencapsulation of Living Cells and Tissues", J. Pharm. Sci. 70, 1981, 351 to 354). While the cells remained viable in culture for up to two months, no experiments are described to test the in-vivo biocompatibility of the polylysine membrane. At approximately the same time, there was reported for the first time, the use of microencapsulated islets to correct the diabetic state of diabetic animals, in F. Lim and A. M. Sun, "Microencapsulated Islets as Bioartificial Pancreas", Science, 210, 1980, 908 to 909. However, the microcapsules, consisting of an inner alginate core, followed by a polylysine coat and an outer polyethyleneimine membrane, were rejected by an animal body within 2 to 3 weeks of implantation due to the poor biocompatibility of the outer polyethyleneimine membrane.

Formation of the latter microcapsules also is described in U.S. Pat. No. 4,352,883 F. Lim. As set forth therein, finely divided living tissue is suspended in an aqueous medium which contains sodium alginate, the suspension is formed into droplets of a size to envelop tissue, the droplets are gelled by conversion to calcium alginate to form discrete, shape-retaining temporary capsules, a permanent semi-permeable membrane is formed about the temporary capsules, and the calcium alginate gel is reliquified within the membrane by ion exchange. Example 3 of the patent describes injection of the microcapsules into diabetic rats.

In the Lim patent, it is indicated that, proteins or polypeptide cross-linkers, such as, polylysine, are readily attacked in vivo resulting in rapid destruction of the membrane whereas cross-linkers which are not readily digestible in mammalian bodies, result in longer lasting membranes. Example 1 of the Lim patent discloses the use of polyethyleneimine and polylysine to form the semipermeable membrane and the article of Lim and Sun mentioned above shows that such microcapsules do not possess an in vivo life of more than two to three weeks.

The parent application Ser. No. 953,413 of the application which lead to the Lim patent contains an Example 1 which uses polylysine as the sole membrane polymer. Although in vitro test results are given, no in vivo studies are specified. No reliquification step is specified in this Example.

The Lim patent discloses that it may be desirable to treat the microcapsules so as to tie up free amino groups which otherwise would impart to the capsules a tendency to clump, by immersing the capsules in a solution of sodium alginate.

Example 1 of the patent discloses immersion of the microcapsules in alginic acid solution. Example 1 of the parent application discloses immersion of the microcapsules in a 0.1% sodium alginate solution. The capsules can be engineered to have a selected in vivo useful life by astute selection of the cross-linking polymer. Proteins or polypeptide crosslinkers, e.g., polylysine, are readily attacked in vivo resulting in relatively rapid destruction of the membrane. Cross-linkers not readily digestible in mammalian bodies, e.g., polyethyleneimine, result in longer lasting membranes." As is apparent from the results achieved by Lim and Sun,referred to above using microcapsules comprising membranes including polyethyleneimine, the organ replacement therapy lasts for a period no longer than about three weeks.

U.S. Pat. No. 4,352,883 mentions the possibility of using polylysine, a much more biocompatible material, instead of polyethyleneimine as the membrane. Polylysine is positively charged and it is well known that positively-charged surfaces are excellent substrates for cell growth. Cell growth on the surface of the microcapsules, such as would occur with a polylysine membrane, would transform the semipermeable capsular wall to an impermeable one, resulting in the death of the encapsulated tissue.

It is apparent, therefore, that there is a need for the development of microcapsules which can be implanted into an animal body and be effective in the treatment of diseases requiring organ transplantation, such as, diabetes, for extended periods of time.

SUMMARY OF INVENTION

In accordance with the present invention, it has now surprisingly been found that, in contrast to the results disclosed in the Lim patent, living cells can be microencapsulated and the resulting microcapsules have long term in vivo activity by encapsulating the cells within a biocompatible semi-permeable membrane which has an outer surface of biocompatible negatively-charged material.

The present invention, therefore, provides biocompatible microcapsules suitable for implantation in a mammalian body comprising encapsulated viable tissue or individual cells within a biocompatible semi-permeable membrane having a biocompatible negatively-charged surface. While the present invention has particular application to the microencapsulation of living cells, any desired macromolecular core material may be provided in the form of microcapsules, such as, enzymes, immunoproteins and activated carbon particles. The macromolecular core material is surrounded by a biocompatible semi-permeable membrane which is permeable to small molecules for contact with the core material but is impermeable to the core material, and also to potentially deleterious large molecules.

In the present invention, the semi-permeable membrane is formed from polylysine. It is essential for the present invention for the polylysine to have a molecular weight of in the range of about 10,000 to about 30,000, preferably about 15,000 to about 25,000, particularly about 17,000 daltons. A polylysine polymer of molecular weight about 35,000, as specifically disclosed by Lim, produces a membrane which is too porous or permeable, such as may permit antibodies to pass therethrough. The lower molecular weight used herein produces a lesser porosity (lower molecular weight cut-off) but satisfactorily permits the ingress of nutrients into the core. A molecular weight below about 10,000 is unsatisfactory since the microcapsule wall cannot form. In the present invention, the polylysine membrane has a molecular weight cut-off below about 150,000 daltons, preferably below 67,000 daltons to allow for a suitable margin of safety should the permeability of the microcapsules change with time.

Another critical feature of the invention is the length of time for which reaction of the capsules with the polylysine occurs. It has been found that a reaction time of at least about 6 minutes and up to about 9 minutes is required to achieve a thickness of membrane which provides sufficient durability, in terms of structural strength and flexibility, to permit injection of the capsules into the body. Example 1 of the Lim parent application Ser. No. 953,413 discloses a reaction time of 2 minutes, which is unsuitable to achieve capsules having the strength and flexibility to permit routine injection. The reaction time produces a membrane which is fragile, which is disclosed in a the Tze et al article.

Another important facet of this invention is that the polylysine membrane is treated to form a negatively-charged outer surface. As discussed below, this is preferably achieved by treatment of the membrane with sodium alginate.

The microcapsules which are provided in accordance with the present invention are biocompatible and, can survive for extended periods of time, up to a year, in rats.

The applicants have found that it is possible to provide microencapsulated islets of Langerhans in a semi-permeable membrane based on polylysine which can survive for surprisingly long periods of time, by the selection of specific critical parameters, as discussed above.

GENERAL DESCRIPTION OF INVENTION AND DESCRIPTION OF PREFERRED EMBODIMENTS

In the present invention, core material, such as, living tissue, individual cells or biologically-active materials, is encapsulated in a biocompatible semi-permeable membrane, in the form of a hydrogel. The material to be encapsulated is suspended in a physiologically-compatible medium containing a water-soluble substance which can be reversibly gelled to provide a temporary protective environment for the tissue. The medium is formed into droplets containing the tissue and gelled, for example, by changing conditions of temperature, pH or ionic environment, to form temporary capsules, preferably of substantially perfect spherical shape, so as to provide an overall improved physical strength when compared with microcapsules formed from non-spherical capsules. Thereafter, the temporary capsules which result are treated to form a membrane of controlled permeability about the shape-retaining temporary capsules. The semi-permeable nature of the membrane permits nutrients and oxygen to flow to the core material and metabolic products to flow therefrom while retaining the core material within the microcapsule. The biocompatible nature of the semi-permeable membrane allows the passage of such materials to and from the core to occur without inflammation or other adverse body response while the outer negatively-charged surface inhibits surficial cell growth, so that the membrane remains semi-permeable and effective for extended periods of time, typically from three to six months or longer.

The temporary capsules may be formed from any non-toxic water-soluble substance that can be gelled to form a shape retaining mass by a change of conditions in the medium in which it is placed, and also comprises plural groups that are readily ionized to form cationic groups. The presence of such groups enables surface layers of the capsule to cross-link to produce a permanent membrane when exposed to polymers containing multiple functionalities of the opposite charge.

Preferably, the temporary capsules are formed from a polysaccharide gum, which may be natural or synthetic, of a type that can be gelled to form a shape retaining mass by exposure to a change in conditions and can be permanently cross-linked or hardened by polymers containing amino groups, which can react with the acidic polysaccharide constituents. Most preferably, the gum is alkali metal alginate, specifically sodium alginate, although other water-soluble gums may be used.

The temporary capsules may be formed from sodium alginate by extruding droplets of aqueous sodium alginate solution into an aqueous calcium chloride solution. As noted above, it is preferred that the temporary capsules be substantially spherical and it has been found that substantially perfectly spherical temporary capsules can be formed by using an aqueous sodium alginate solution having a viscosity of at least about 30 centipoise. At viscosities below this critical lower limit, the temporary capsules have an irregular shape. Perfectly spherical capsules are obtained over a wide range of viscosity of the sodium alginate solution, with an upper limit being dictated largely by the ability to extrude the solution into the hardening medium. Usually, the viscosity of the aqueous sodium alginate solution does not exceed about 1000 cps.

Formation of the permanent semi-permeable membrane about the temporary capsules preferably is effected by ionic reaction between free acid groups is the surface layer of the gelled gum and biocompatible polymers containing amino groups, typically in a dilute aqueous solution of the selected polymer.

The cross-linking biocompatible polymer which is used is a polylysine having a molecular weight within a specific range. It is noted that polyethyleneimine and other imine-containing polymers are unsuitable for membrane formation in view of their non-biocompatible nature. As noted earlier, in accordance with this invention, the molecular weight of the polylysine polymer must be controlled within a narrow range of about 10,000 to about 30,000, preferably about 17,000, to achieve the required porosity. The use of polylysine results in microcapsules having a positively-charged surface, which, as already noted, would be unsuitable for long term viability. As also noted above, it is important for long term in vivo life for the polylysine to be reacted for a period of time sufficient to develop a membrane with sufficient structural strength and flexibility to permit in vivo injection and sufficient quantity of biocompatible polymer to permit in vivo structural integrity to be retained. Usually, a reaction time of at least six minutes is required to achieve these results, generally up to about nine minutes. A reaction time of less than about 6 minutes produces a thin-walled and fragile capsule while a reaction time of greater than about 9 minutes produces a thick-walled less flexible and more rigid capsule. A reaction time from about 6 to about 9 minutes produces a capsule with optimum strength and flexibility.

Surprisingly, the actual strength of the aqueous solution of polylysine used to react with the temporary capsules does not affect the capsule wall thickness, at concentration levels in excess of about 0.05 wt.%.

The semi-permeable membrane formed about the temporary capsules by the reaction with the polylysine next is treated with a non-toxic biocompatible water-soluble polymeric material which is capable of ionic reaction with free amino groups to form an outer negatively-charged coating about the membrane, typically by suspension of the microcapsules in an aqueous solution of the polymeric material. The material used to form the outer coating preferably is the same material as is used to form the temporary capsules, preferably a polysaccharide gum, more preferably an alkali metal alginate, such as, sodium alginate. Other biocompatible polymeric materials containing base-reactive groups, such as, polyvinyl alcohol and poly beta-hydroxy butyric acid, may be used to form the outer coating to the microcapsules. Molecular weights of such polymeric materials typically vary from about $10^4$ to about $10^6$.

The biocompatible water-soluble polymeric material containing amino-reactive groups reacts with the outer amino-groups of the semi-permeable membrane to form an outer coating. This outer coating shrouds the polylysine layer, although leaving intact the porosity of the semi-permeable membrane, and provides a negatively-charged surface. By virtue of the number of surface amino groups on the polylysine membrane, resulting from the prolonged reaction time utilized herein, the outer negatively-charged polymer coating resists degradation and removal, in vivo, so that the positively charged surfaces are not exposed to the body environment.

The treatment of the polylysine microcapsules with the biocompatible base-reactive material retains the overall biocompatible nature of the semi-permeable membrane and results in a negatively-charged outer surface which inhibits cell growth and, therefore, permits the semi-permeable membrane to retain its permeability and hence effectiveness over an extended period of time.

Following formation of the microcapsules, reliquification of the suspending medium for the core material may be effected by re-establishing the conditions under which the material is liquid. This may be achieved by ion exchange to remove multivalent cation, for example, by immersion in phosphate buffered saline or citrate buffer. The reliquification step, though beneficial in decreasing diffusion resistance, is not essential for the provision of an effective product and may be omitted, since it has been shown that transplanted islets (rate to mouse) in microcapsules whose interiors have not been reliquified, are also effective in normalizing blood sugar levels of diabetic animals. Surprisingly, the calcium alginate gel core does not reliquify inside the body, since intact gel cores have been found in microcapsules recovered from diabetic animals up to one year after implantation.

The process of the invention may be used to encapsulate living tissue, multicellular fractions thereof or individual cells, for example, islets of Langerhans, liver cells and red blood cells, and other biologically-active material. The microcapsules which result may be implanted into an appropriate site within a mammalian body for the purpose of providing the body with the specialized physiological function of the tissue while the tissue remains viable. The implantation may be achieved by simple injection, so that surgical procedures are not required.

The core of the microcapsules contains the living tissue cells and an aqueous medium of nutrients sufficient to maintain the tissue and allow its normal metabolism. The cells are viable, physiologically active and capable of ongoing metabolism.

The biocompatible semi-permeable membrane encapsulating the core material consists of interpenetrating layers of ionically-interacted biocompatible materials. The overall wall thickness of the semi-permeable membrane usually is about 5 $\mu$m. The microcapsules themselves have a diameter in the range of about 500 to about 2000 $\mu$m, usually in the range of about 700 to about 1000 $\mu$m for microcapsules containing islets of Langerhans as the core material. The biocompatible semi-permeable membrane is in the form of a hydrogel and hence has an overall water content within the membrane structure of at least about 20 wt% which may vary up to about 95 wt% depending on the molecular weight of the amino acid.

Such PEI-containing membranes, however, have been shown to result in microcapsules which remain operative for only two to three weeks in vivo. It is entirely unexpected, therefore, on the basis of the teachings of the Lim patent, that one could increase the in vivo life dramatically, as achieved herein, by using polylysine of particular molecular weight range within the specific process conditions recited herein, with posttreatment of the polylysine membrane with sodium alginate.

The in-vivo survival time which has been observed for the products of this invention is a significant period of time and a considerable advance in the art. The potential for long term control of diabetes in humans using microencapsulated islets of Langerhans is demonstrated by the in vivo results obtained in rats, although no clinical trials have yet been conducted involving humans.

In a particularly preferred embodiment of the invention, living cells are microencapsulated within a polylysine-alginate semi-permeable hydrogel. The cells are initially suspended uniformly in a sodium alginate solution in physiological saline. Where the microcapsules are to be used for the treatment of diabetes by controlling blood sugar in animals, including humans, the living cells take the form of islets of Langerhans from an animal pancreas.

Spherical droplets containing the cells are produced from an aqueous sodium alginate solution by a droplet generator, such as, syringe pump air jet extrusion, and are collected as gelled spheres in a hardening solution, such as, calcium chloride. The gelled spheres are coated with polylysine followed by an outer coating of sodium alginate. The microcapsules may then be suspended in isotonic sodium citrate or other convenient ion exchange medium to reliquify the alginate gel inside the microcapsule to restore the cells to a mobile state. As noted earlier, this step may be omitted, if desired.

The outer biochemically inert but biocompatible alginate surface is a negatively-charged hydrogel containing up to about 95% water. The low interfacial tension between the swollen gel surface and the aqueous biological environment minimizes protein interaction, otherwise a strong protein-polymer interaction may cause a severe inflammatory response. The biocompatibility of the hydrogel membrane leads to long term viability of the capsules when implanted. Polyethyleneimine-surfaced microcapsules do not appear to possess this property and hence are rejected by the body and produce a strong inflammatory response, which severely limits the useful life of the microcapsules within the body. The soft rubbery consistency of most hydrogels may also contribute to their biocompatibility by decreasing frictional irritation to surrounding tissues.

The strength of the microcapsules may be increased by additional cross-linking, for example, using glutaraldehyde, prior to reliquification of the gel, if effected.

In the present invention, it is not essential that the biocompatible outer surface be composed of sodium alginate, but it is essential that the outer surface be biocompatible and negatively-charged. Binding occurs between the negatively-charged groups, usually hydroxyl or carboxyl groups, of the biocompatible outer surface material, and the positively-charged amino groups on the polylysine.

By the present invention, therefore, there have been obtained biocompatible microcapsules which have long term in-vivo life and hence are particularly suited to the implantation of living tissue which are capable of ongoing metabolism. The microcapsules of the invention, although particularly useful for in-vivo implantation, also may be put to a variety of in-vitro uses.

Such in-vitro uses include utilization of microencapsulated islet cells or other tissue cells to produce metabolic products, such as, in situ, in a culture medium and utilization of microencapsulated microbial cells as efficient bioreactors for the production of biochemicals and proteins, such as, ethanol and penicillin.

EXAMPLES

Example 1

This Example illustrates the microencapsulation of islets of Langerhans.

Cultured rat islets of Langerhans ($2 \times 10^3$ islets in 0.2 ml medium) were suspended uniformly in 2 ml of a 1.5% (w/w) sodium alginate solution (viscosity 51 cps) in physiological saline. Spherical droplets containing islets were produced by syringe pump/air jet extrusion through a 22-gauge needle and collected in 1.5% (w/w) calcium chloride solution. The supernatant was decanted and the gelled spherical alginate droplets, containing islets, were washed with dilute CHES (2-cyclohexylamino-ethane sulfonic acid) solution and 1.1% calcium chloride solution.

After aspirating off the supernatant, the gelled droplets were incubated for 6 minutes in 0.05% (w/w) polylysine having a molecular weight of 17,000.

The supernatant was decanted and the polylysine capsules were washed with dilute CHES, 1.1% calcium chloride solution and physiological saline. The washed polylysine capsules were incubated for 4 minutes in 30 ml of 0.03% sodium alginate to permit the formation of an outer alginate membrane on the initial polylysine membrane, by ionic interaction between the negatively charged alginate and the positively charged polylysine.

The resulting microcapsules were washed with saline, 0.05M citrate buffer for 6 minutes to reliquify the inner calcium alginate, and a final saline wash. The microcapsules were found to be perfectly spherical and each to contain from 1 to 2 viable islets. The microcapsules had diameters of $700 \pm 50$ μm and wall thicknesses of about 5 μm. The microcapsules were suspended in nutrient medium at 37° C.

The experiment was repeated with islet cells from mouse, bovine and dog pancreas and similar microencapsulated products were formed.

Example 2

This Example illustrates the viability of the microencapsulated islets.

In perifusion experiments, the insulin secretion from the microencapsulated rat islets produced in accordance with the procedure of Example 1 was determined to be comparable with that from unencapsulated islets. When the glucose concentration was raised from 50 to 300 mg, there was a biphasic response of insulin release from both groups of islets and the insulin secretion increased.

The increase in the quantity of insulin in the presence of a high glucose concentration clearly demonstrated that the viability and functionality of the cells were retained throughout the process of microencapsulation.

After 2 months in culture at 37° C., the microencapsulated islets were observed to have remained morphologically and functionally intact.

Example 3

This Example illustrates the injection of microencapsulated islets into diabetic rats.

Diabetic rats with blood glucose levels in the range of 370 to 470 mg/dL were treated with approximately $3 \times 10^3$ rat islets microencapsulated as set forth in Example 1 with the exception that polylysine having a molecular weight of 25,000 daltons was used. The microcapsules were introduced by injection into the peritoneal cavity using a canula fitted to a syringe.

Unencapsulated islets and islets microencapsulated in a polylysine-polyethyleneimine membrane, produced as described in U.S. Pat. No. 4,352,883 (Lim), were used as controls. Blood glucose levels were assayed twice per week to determine the period of time for which the blood glucose level was lowered. The results obtained as set forth in the following Table I:

TABLE I

| Membrane Type | Number of Weeks Blood Glucose Level Lowered | |
|---|---|---|
| None | 1 | (N = 4) |
| Polylysine polyethyleneimine (Lim Patent) | 2 to 3 | (N = 8) |
| Polylysine alginate (Present invention) | 13 to 52 | (N = 10) |

As can be seen from the results of Table I, the islets enclosed in the biocompatible polylysine alginate membranes of the invention survived up to 52 weeks, as demonstrated by the normal fasting blood sugar levels in the diabetic rats. In contrast, the islets enclosed in the polylysine-polyethyleneimine capsular membranes of the Lim Patent showed survival times of less than 3 weeks.

Example 4

This Example shows the effect of multiple injections of microencapsulated islets.

The procedure of Example 3 was repeated except that, following a return to hyperglycemia (blood sugar concentration greater than 300 mg/dL), a second injection of polylysine alginate microencapsulated islets produced in accordance with the procedure of Example 1, using polylysine of molecular weight of 25,000 daltons, normalized the blood sugar level of the animal for a longer period than the initial injections, allowing the blood sugar level of the diabetic rats to be controlled for longer than six months with just two injections.

In contrast, five injections of polylysine-polyethyleneimine microencapsulated islets at 2 to 3 week intervals were barely able to control the blood glucose level of diabetic animals for three months (N=8).

Example 5

This Example illustrates the injection of microencapsulated rat islets into diabetic mice.

The procedure of Example 3 was repeated except that fewer islets were used (1000 rat islets), diabetic mice were employed and the liquification step was omitted. No polylysine polyethyleneimine microcapsules were used as controls.

Blood sugar levels in the diabetic mice were controlled for more than two months with a single injection (I.P.), indicating that xenograft transplants (cross-species) are possible. In addition, these results show that reliquification of the alginate gel inside the capsules is not essential.

Example 6

This Example illustrates the viability of recovered microencapsulated transplanted islets.

Microencapsulated islets were recovered from some of the treated diabetic rates in Example 3 at 3, 5 and 12 months postimplantation. The majority of the microcapsules were still physically intact and contained viable insulin-secreting islets, as demonstrated by secretion of insulin from the recovered islets in culture in response to a high glucose concentration.

Example 7

This Example illustrates the microencapsulation of liver cells.

The procedure of Example 1 was repeated, except that fetal mouse liver cells were employed in place of islets. Capsules containing viable liver cells were obtained, as determined by trypan blue exclusion and a histological study. Each capsule was observed to contain several thousand liver cells.

Example 8

This Example illustrates the use of polyvinyl alcohol as the external surface of the microcapsules.

The procedure of Example 1 was repeated, except that 1.0% (w/w) solution of polyvinyl alcohol in phosphate buffered saline was used in place of the sodium alginate solution for formation of the outer membrane coating. The polyvinyl alcohol did not significantly alter the permeability of the capsular membrane.

Polyvinyl alcohol is known to be a biocompatible water-soluble polymer and has been used in many surgical applications, such as, thromboresistant coatings for artificial blood vessels, and hence the microcapsules produced in this Example are expected to exhibit similar blood sugar decreasing capability in diabetic animals to the microcapsules produced by the procedure of Example 1.

Example 9

This Example illustrates the use of polylactic acid as the external surface of the microcapsules.

The procedure of Example 1 was repeated, except that 0.1% (w/w) solution of polylactic acid in buffered saline was used in place of the sodium alginate solution for formation of the outer membrane coating. The polylactic acid was initially dissolved in dilute sodium hydroxide and then neutralized with hydrochloric acid. The ongoing viability of the islets in the microcapsules so produced was demonstrated with trypan blue staining. Polylactic acid is a biocompatible polymer that is currently in clinical use as suture material. It is expected, therefore, that the microcapsules produced in this Example will exhibit similar blood sugar decreasing capability in diabetic animals to the microcapsules produced by the procedure of Example 1.

Example 10

This Example illustrates the preparation of spherical calcium alginate droplets.

Sodium alginate solutions of varying concentrations (and hence viscosities) were extruded with a syringe pump/air jet (22 gauge needle) into a 1.5% (w/w) calcium chloride hardening solution and the resulting gel droplets were collected and their physical shape observed. The results are reproduced in the following Table II:

TABLE II

| Sodium Alginate % (w/w) | Viscosity (cps) | Fractions of Droplets which are Spherical (%) |
|---|---|---|
| 1.5 | 51 | 100 |
| 1.4 | 43 | 100 |
| 1.3 | 36 | 100 |

TABLE II-continued

| Sodium Alginate % (w/w) | Viscosity (cps) | Fractions of Droplets which are Spherical (%) |
| --- | --- | --- |
| 1.2 | 30 | 100 |
| 1.1 | 25 | 25 |
| 1.0 | 20 | 0 |
| 0.9 | 16 | 0 |
| 0.7 | 11 | 0 |
| 0.3 | 4 | 0 |

While in all instances, the droplets could be broadly described as "spheroidal", it will be apparent from Table II that it is only at concentrations of sodium alginate solution of 1.2% w/w and above, i.e. viscosities of 30 cps and above, that perfect spheres are formed.

Example 11

This Example illustrates the preparation of microcapsules using parameters outside the critical range.

The procedures of Example 1 were repeated except that the islets were omitted and the molecular weight of the polylysine was varied. Polylysines with molecular weights outside the critical range of 10,000 to 30,000 daltons were employed. Microcapsules were also prepared with polylysine of molecular weight within the critical range as references.

It was found that permanent microcapsules could not be prepared with polylysine of molecular weight of 4,000 daltons, the capsules dissolving in the liquification step. Microcapsules formed from polylysine of molecular weight 40,000, 90,000 and 400,000 were more fragile than the reference microcapsules produced with polylysine of molecular weight 17,000 and also had molecular weight cut-offs greater than 67,000 daltons since they were permeable to bovine serum albumin and haemoglobin.

The results obtained are summarized in the following Table III:

TABLE III

| Polylysine Molecular Weight (daltons) | Microcapsule Formation | Capsule Wall thickness ($\mu$m) Dry | Capsule Wall thickness ($\mu$m) Wet | Water Content % H$_2$O | Molecular Weight Cut-off (daltons) | Capsule Durability[1] |
| --- | --- | --- | --- | --- | --- | --- |
| 4,000 | No | — | — | — | — | — |
| 17,000 | Yes | — | — | — | <67,000 | +++ |
| 25,000 | Yes | 0.86 | 5.23 | 83 | — | +++ |
| 40,000 | Yes | — | — | — | >67,000 | +++ |
| 90,000 | Yes | 0.26 | 6.24 | 96 | >67,000 | ++ |
| 400,000 | Yes | — | 5.38 | — | >67,000 | + |

Note [1] +++ strong and flexible → + very fragile

Example 12

This Example illustrates increasing the strength of the microcapsules.

The procedures of Examples 1, 8 and 9 were repeated, except that the microcapsules were placed in contact with 0.01% w/w glutaraldehyde for less than 60 seconds, just after the polylysine coating step or just before the citrate washing step. The microcapsules which result are more difficult to break physically (using fine tweezers) and also are more difficult to dissociate in a heparin solution, when compared with un-cross-linked material.

SUMMARY OF DISCLOSURE

In summary of this disclosure, the present invention provides novel microcapsules of living tissue or cells which have long term biocompatibility and viability, and hence utility, in the treatment of diseases requiring organ transplantation, such as, diabetes. Modifications are possible within the scope of the invention.

What we claim is:

1. A microcapsule having a diameter of about 500 to about 2000 $\mu$m and suitable for implantation into an animal body, comprising:
   a core comprising one or more viable, healthy, physiologically-active tissue cells capable of ongoing metabolism, and
   a biocompatible semi-permeable membrane surrounding and enclosing said core, said semi-permeable membrane being permeable to tissue nutrients and metabolic products produced by the tissue but impermeable to immune system proteins, said semi-permeable membrane having a molecular weight cut-off of below about 150,000 daltons,
   said biocompatible membrane being a hydrogel formed by ionic reaction between a polylysine polymer having a molecular weight from about 10,000 to about 30,000 daltons and a polymeric material bearing negatively-charged groups to provide an outer negatively-charged surface,
   said polylysine polymer membrane having a durability sufficient to permit said microcapsules to be injected in the animal body and sufficient to maintain said microcapsules in an intact form and to permit said tissue to effect ongoing metabolism when injected into the animal body for a period of time exceeding three months.

2. The microcapsule of claim 1 wherein said tissue cells are islets of Langerhans.

3. The microcapsule of claim 1 wherein said negatively charged groups are carboxyl or hydroxyl groups.

4. The microcapsule of claim 3 wherein said polymeric material bearing negatively charged groups is selected from the group consisting of alginate, polyvinyl alcohol or polylactic acid.

5. The microcapsule of claim 4 wherein said polylysine has a molecular weight of about 15,000 to about 25,000.

6. The microcapsule of claim 5 wherein said polylysine has a molecular weight of about 17,000.

7. The microcapsule of claim 1 having a diameter of about 700 to about 1000 $\mu$m and wherein said semi-permeable membrane has a thickness of about 5 $\mu$m.

8. The microcapsule of claim 1 wherein said membrane has a molecular weight cut-off of about 67,000 daltons.

9. The microcapsule of claim 1 wherein said core also comprises an aqueous medium of nutrients sufficient to maintain said tissue cells and allow normal metabolism thereof.

10. A method of encapsulating a core material within a semi-permeable membrane to form microcapsules for implantation into an animal body, which comprises:

(a) placing the material in an aqueous solution of a water-soluble polymeric substance that can be reversibly gelled and which has free acid groups, (b) forming the solution into droplets, (c) gelling the droplets to produce discrete shape-retaining temporary capsules, (d) forming semi-permeable membranes about the temporary capsules by contact between the temporary capsules and a polymer containing free amino groups to cause ionic reaction with the acid groups in a surface layer of the capsule, said polymer containing free amino groups being polylysine having a molecular weight of about 10,000 to about 30,000 daltons, said contact being effected for a period of time no less than about four minutes sufficient to provide a polymer coating on the temporary capsule of sufficient durability to permit the microcapsules to be injected into the animal body, and (e) contacting said microcapsules formed in step (d) with a biocompatible polymeric material which contains free negatively-charged groups capable of ionic reaction with the free amino groups in a surface layer of the microcapsule, thereby to form an outer coating of said biocompatible polymeric material on said microcapsules.

11. The method of claim 10 wherein said core material comprises living tissue which is in finely-divided suspended form in said aqueous solution in step (a).

12. The method of claim 11 wherein said living tissue comprises islets of Langerhans whereby said microcapsules may be used to control blood sugar levels in diabetic animal bodies into which the microcapsules are implanted.

13. The method of claim 10 wherein said reversibly-gellable water-soluble substance is a polysaccharide gum.

14. The method of claim 13 wherein said gum is an alkali metal alginate.

15. The method of claim 10 wherein said polylysine has a molecular weight of about 15,000 to about 25,000 daltons.

16. The method of claim 10 wherein said contact in step (d) is effected for a period of time sufficient to provide a polylysine layer of thickness about 5 μm.

17. The method of claim 10 wherein said contact in step (d) is effected by contact with an aqueous solution of polylysine at about 6 to about 9 minutes.

18. The method of claim 17, wherein said aqueous solution of polylysine has a concentration of at least about 0.05 wt.%.

19. The method of claim 10 wherein said biocompatible negatively-charged polymeric material is selected from the group consisting of polyvinyl alcohols having free hydroxyl groups and polylactic acids containing free acid groups.

20. The method of claim 10 wherein said reversibly-gellable water-soluble substance comprises sodium alginate, and said biocompatible polymeric material comprises sodium alginate.

21. The method of claim 14 wherein said alkali metal alginate is sodium alginate and the viscosity of said aqueous solution of sodium alginate is at least sufficient to result in the formation of substantially spherical temporary capsules.

22. The method of claim 21 wherein said aqueous sodium alginate solution has a viscosity of at least about 30 cps.

23. The method of claim 10 including the further step of reliquifying the gel within the semi-permeable membrane.

24. A tissue implantation method, which comprises:
encapsulating tissue within a spherical microcapsule having a diameter of about 500 to about 2000 μm and a biocompatible semipermeable membrane having a negatively-charged biocompatible outer surface and a thickness of about 5 microns, said biocompatible membrane having a molecular weight cut-off below 150,000 daltons and being impermeable to immune system proteins but permeable to tissue nutrients and metabolic products produced by the tissue, said biocompatible semipermeable membrane being a hydrogel formed by ionic reaction between a polylysine polymer having a molecular weight from about 10,000 to about 30,000 daltons and a polymeric material being negatively charged groups and further comprising an outer, negatively charged surface and
introducing said microcapsule into a mammalian body to effect ongoing metabolism in said body for a period of time exceeding three months.

25. The method of claim 24 wherein said microcapsule is introduced by injection.

26. The method of claim 24 wherein said tissue comprises islets of Langerhans or a fraction thereof.

27. The method of claim 24 wherein said microcapsule is substantially perfectly spherical.

28. The method of claim 24 wherein said tissue comprises liver cells.

29. The method of claim 24 wherein said membrane has a molecular weight cut-off of less than about 67,000 daltons.

* * * * *